(12) United States Patent
Brooke et al.

(10) Patent No.: US 6,328,992 B1
(45) Date of Patent: *Dec. 11, 2001

(54) CANNABINOID PATCH AND METHOD FOR CANNABIS TRANSDERMAL DELIVERY

(76) Inventors: Lawrence L. Brooke, 3691 Frei Rd., Sebastopol, CA (US) 95472; Cal C. Herrmann, 5621 Sierra Ave., Richmond, CA (US) 94805; Su IL Yum, 1021 Runnymead Ct., Los Altos, CA (US) 94024

( * ) Notice: Subject to any disclaimer, the term of this patent is extended or adjusted under 35 U.S.C. 154(b) by 0 days.

This patent is subject to a terminal disclaimer.

(21) Appl. No.: 09/655,634

(22) Filed: Sep. 5, 2000

Related U.S. Application Data

(63) Continuation-in-part of application No. 09/056,848, filed on Mar. 3, 1998, now Pat. No. 6,113,940
(60) Provisional application No. 60/039,603, filed on Mar. 3, 1997.

(51) Int. Cl.⁷ ............................... A61F 13/00; A61K 9/70
(52) U.S. Cl. ..................... 424/449; 424/443; 424/447; 424/448
(58) Field of Search ................................ 424/448, 449, 424/443, 447

(56) References Cited

U.S. PATENT DOCUMENTS 6,113,940 * 9/2000 Brooke et al. ................. 424/449

* cited by examiner

Primary Examiner—Thurman K. Page
Assistant Examiner—S. Howard
(74) Attorney, Agent, or Firm—Kenneth J. Hovet

(57) ABSTRACT

A transdermal structure is provided for delivering cannabis chemical(s) to one's bloodstream. The structure comprises a backing layer which carries the cannabis chemical(s). The chemicals are contained in a film on the backing layer or within a cavity formed in the backing layer. Alternatively, an opening in a secondary layer that overlies the backing layer may be used to create the cavity. The structure is applied to one's skin so that the cannabis chemicals are in contact with the skin. A polymer material which is mixed with the cannabis and placed in the cavity or a membrane over the cavity may be used to control the flow of cannabis chemical(s) into the bloodstream. In an alternative embodiment, a porous material impregnated with cannabis chemical(s) may be used to hold the chemical(s) in the cavity. Because of the relatively slow transdermal flow rate of cannabis materials, it is preferred to utilize permeation enhancers in conjunction with the cannabis carrier or reservoir matrixes or skin contacting adhesive layers.

27 Claims, 1 Drawing Sheet

CANNABINOID PATCH AND METHOD FOR CANNABIS TRANSDERMAL DELIVERY

This application is a Continuation-In-Part of application Ser. No. 09/056,848 filed Mar. 3, 1998, now U.S. Pat. No. 6,113,940 which claims priority from Provisional Application No. 60/039,603 filed Mar. 3, 1997.

FIELD OF THE INVENTION

This invention pertains to methods and products for the transdermal administration of cannabis. More particularly, this invention concerns a system for delivering effective dosages of cannabis to one's bloodstream.

BACKGROUND OF THE INVENTION

Methods and products for transdermally administering particular chemicals are known in the art. Several U.S. patents have issued for the transdermal application of chemicals, most recently for nicotine. This invention expands the concept of transdermal delivery to cannabis, since the unique social and chemical characteristics of cannabis lend it to such an application.

Several medicinal uses have been found for the active ingredients of cannabis, including the ingredients tetrahydrocannabinol (THC), cannabinol (CBN), cannabidiol (CBD) and cannabichromene (CBC). The medicinal uses of cannabis include (1) treatment of nausea and pain associated with cancer and chemotherapy; (2) nausea, pain and wasting associated with AIDS; (3) arthritis and rheumatism; (4) glaucoma; (5) migraines; (6) muscle spasticity associated with multiple sclerosis and paralysis; (7) alcohol and narcotics withdrawal; (8) stress and depression; (9) asthma; and (10) epileptic seizures. Despite the many proven or suspected benefits of cannabis, legal and social barriers prevent its widespread use. Currently, only Marinol, a synthetic form of THC is available by prescription to patients. One purpose of the present invention is to extend the widespread medicinal use of cannabis without triggering the legal or social barriers associated with prescription of the drug.

The chemical composition of cannabis and its active ingredients allow for its transdermal delivery. For instance, the primary active ingredient of cannabis is THC, which is effective in vivo at very low doses. Due to its high liphophilicity, THC exhibits strong tendency to bind to tissue and protein, making transdermal application difficult. Fatal misuse has also been a concern in previous transdermal applications, but cannabinoids are rarely fatal when overdosed. Furthermore, THC is rapidly metabolized in the body, such that concentration levels of the chemical in the bloodstream decreases rapidly if administered through traditional methods. In contrast, a transdermal application allows for small dosages of THC to be administered over an extended period of time, thereby allowing the concentration levels of the chemical to remain relatively steady in the bloodstream.

SUMMARY OF THE INVENTION

The present invention comprises a structure, such as a skin patch, bandage, covering or related assembly of materials, which can contain and administer an effective amount of cannabis or its chemical constituents during a predetermined period of time. One purpose of the structure is to allow for controlled delivery of the active chemicals, such that plasma levels of the chemicals may be controlled in a safe, convenient and effective manner for the patient.

This invention also comprises the method of treating a patient with a transdermal cannabis preparation. Most conveniently, this is accomplished by application of the transdermal structure described herein. Antecedent or conjunctive steps for increasing the permeability of the patient's skin may further comprise the method for transdermally applying cannabis.

The invention includes a reservoir means for retaining and dispersing the active ingredients of the cannabis. In one embodiment of the invention, the reservoir means includes a rate controlling means overlying a cavity formed in a backing layer containing the cannabis. The rate controlling means regulates flux, hereinafter defined as the diffusion flow rate of the cannabis to the skin.

The rate controlling means may comprise a nonporous polymer membrane for regulating the flux. Alternatively, the rate controlling means may comprise a porous material made of elements suitable for controlling the diffusion rate of cannabis. Examples of suitable porous materials include porous rubber or plastic layers soaked in an aqueous ionic solution.

The reservoir means may also comprise a polymer matrix material which suspends the cannabis and releases it in a controlled manner. The flux of the polymer matrix material may further be regulated by a rate controlling membrane.

DESCRIPTION OF THE PREFERRED EMBODIMENTS

"Cannabis", as used herein, means a cannabis solution which has been preferably extracted from its natural source such as marijuana and hashish, or any one or more compound or chemical component thereof, including tetranydrocannabinol (THC), cannabinol (CB), cannabidiol (CBD) and cannabichromene (CBC). Characteristics of a typical cannabis material useful with the invention are:
1) Solubility of about 2 microgram/ml in water at 37C.
2) Solubility of about 500 milligram/ml or greater in light mineral oil at 37C.
3) Molecular weight ranges from about 300 to 350 gm/mol.
4) Log Po/w (logarithm of octanol/water partition coefficient) range from 5 to 9.

As used herein, the term "oil" comprises any one or mixture of pharmaceutical grade light mineral oils, vegetable oils, fish and animal oils. Examples of vegetable oils are sesame, corn cottonseed, almond, orange, lemon, eucalyptus, olive, peanut, safflower, cinnamon, clove and soybean oils. Other usable oils are cod liver and castor oils. The word "structure" means one or more layers of material suitable for attachment to one's skin, including strips or patches of fabric, plastic, metal foil, rubber, resin film, natural membranes and laminates of any one or combination of the above.

Figure 1:
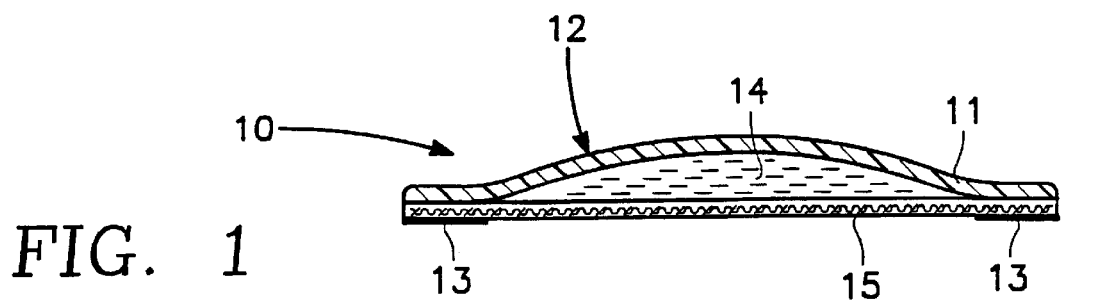
FIG. 1 shows an embodiment of the invention comprising a backing layer, a reservoir of cannabis and a rate controlling membrane.

With reference to FIG. 1, a cannabinoid structure 10 is depicted comprising a backing layer 11, a reservoir means 12 and an adhesive means 13. Since the cannabinoid structure may contain several active ingredients at variable concentrations, including THC and CBD, the listed parameters and specific materials may be varied to accomodate administration of specific ingredients or dosages.

The backing layer 11 functions to protect the contents of the structure from environmental conditions, such as evaporation or abrasion. The backing layer 11 may have multiple linings, with the interior lining adjoining the reservoir means.

To protect the structure while in use, the inner surface of the backing layer should not interact with the cannabis ingredients. For instance, THC should not adjoin silicone-based materials since THC is known to bind with such surfaces. Examples of materials having potential for comprising an effective backing layer include aluminized polyester and nonwoven polyester. Other examples are 3M Product Nos. 1109, 1006, 1009, 1220 and 1012Scotchpak polyester film laminates.

With further reference to FIG. 1, the reservoir means comprises a cavity 12 in the backing layer containing a cannabis preparation 14. A rate controlling membrane 15 overlies the cavity for regulating dispersion of the cannabis chemicals. The cavity comprises a round or oval-shaped convex area in the backing layer. It is sized to accommodate the selected volume of cannabis preparation 14.

The cannabis preparation comprises a liquid or gel carrier combined with the aforementioned oil and the cannabis component(s). The amount of carrier can range from about 10–90 weight percent of the overall preparation and the oil may be present in a range of 1–90weight percent of the preparation.

Other suitable carriers are natural rubber blends, viscoelastic semi-solids such as pressure sensitive adhesive materials, hydrogels, soft thermoplastic polymers such as ethylene vinyl acetate with high VA contents, elastomers such as polyisoprene elastomers and thermoplastic elastomers such as styrene-butadiene block copolymers.

Other effective gel or liquid carriers may include carbon tetrachloride, ethanolic solutions of resin and pyrahexyl mixed with THC, Tween 80 or petrol ether. In all cases, the carrier material should be inert to the cannabis chemicals and permit easy migration of the preparation to the patient's skin.

The rate controlling means is located directly adjacent to the patient's skin. Its function is to control the flux of cannabis from the reservoir to the skin. A preferred rate controlling means may comprise a polymer membrane having a predetermined permeability and thickness for allowing the release of effective amounts of cannabis continuously from several hours to several days.

Once an appropriate polymer is chosen, the membrane may be formed by preparing a homogenous solution containing the polymer and an organic solvent. The solution is cast upon a glass plate or equivalent, where the solvent is evaporated from the solution. The evaporation of the solvent results in a film which comprises the membrane, and the thickness of the membrane can be varied as required by the desired cannabis flux.

Alternatively, the rate controlling membrane may be in film form. The cannabinoid patch may then be prepared by heat sealing the backing layer 11 around the perimeter of the membrane with the cavity in-between.

Factors to consider in determining an appropriate polymer membrane include the polymer's resistance to deterioration from cannabis, and the polymer's permeability towards cannabis. Previous transdermal applications have used dense nonporous materials such as commercial polyethylene (Sclairfilm).

Nonporous polymer materials offer the advantage of administering the drug over the greatest period of time. However, nonporous polymer materials are not necessarily optimally suited for a transdermal cannabinoid structure, since cannabis components have relatively large molecular sizes and exhibit unique chemical interactions such as binding with some materials.

The rate controlling means may also comprise porous materials which are fastened to the backing layer 11 with adhesives, sonic welding or heat sealing techniques. The cavity is then suspended between the backing layer and the porous material. Prior experimentation has shown that cannabis ingredients such as THC diffuse rapidly through certain porous materials such as rubber and plastic.

Furthermore, THC is insoluble with many solutions, including aqueous and ionically charged solutions. An application of an ionic aqueous solution to a porous material will hinder the diffusion rate of THC through the material and decrease flux of cannabis. Therefore, an appropriate combination of porous THC absorbing material, combined with a solution that is insoluble with THC, can form a suitable rate control means. An example of such a rate controlling membrane includes mixing salt water with a porous rubber membrane that covers the cavity. The thickness of the porous rubber membrane, the concentration of the salt water, and the amount of available cannabis in the cavity are optimized experimentally to create a desired flux of THC to the patient's skin. Evaporation of necessary fluids may be prevented by a protective backing layer.

With further reference to FIG. 1, an adhesive means 13 may be integrated with the cannabis assembly to hold the structure in contact with the user's skin. The adhesive means should be compatible with cannabis, and should not hinder movement of the cannabis into the patient's skin. The adhesive means may comprise one or more film strips of pressure-sensitive material, such as an acrylate based adhesive, having amine resistance. The adhesive strips can be cast directly onto the skin-facing side of the backing layer or the rate controlling membrane. Alternatively, medical adhesive tape may simply be applied over the backing layer's outer surface, thereby securing the structure to the skin of the patient.

Figure 2:
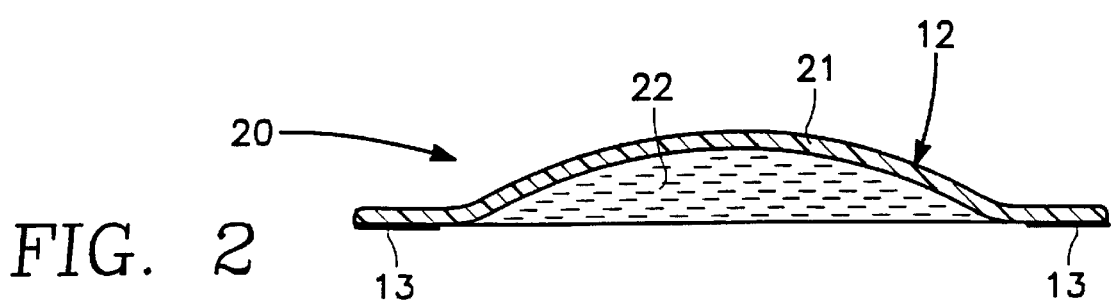
FIG. 2 shows an embodiment of the invention comprising a backing layer with a reservoir of viscous cannabis/polymer material.

With reference to FIG. 2, an alternative structure 20 is shown. This structure is similar to FIG. 1 in that it utilizes a backing layer 21 having a cavity 12. Within the cavity is a matrix composition 22 comprising cannabis suspended in a polymer solution. In this embodiment, the matrix material serves as both the cannabis carrier and the rate controlling diffusion mechanism for administration of the cannabis. As such, use of a rate controlling membrane is not essential.

The matrix composition 22 may be prepared by forming a solution comprising a solvent mixed with a polymer matrix material. Cannabis, preferably in liquid form, is homogeneously mixed with the polymer matrix solution. The concentration of cannabis may be varied depending on the desired chemical load for the specific cannabinoid application. The resulting solution is cast on the backing layer 21 where the solvent is evaporated to create a polymer film. In this variation, the cavity 12 may not be necessary.

The above-mentioned polymer matrix may also be formed apart from the backing layer 21 by attaching a single-sided occlusive medical tape to one face of the matrix material 22. The matrix thickness determines the upper limit of the cannabis concentration or loading per unit area, since overloading the cannabis concentration will prevent the film from forming. Examples of suitable polymers and carrier materials for forming the matrix material include acrylic adhesives, polyurethane., polymethyl methacrylate, polybutyl methacrylate and ethylene-acrylic acid polymers. Suitable solvents include tetrahydrofuran, dimethysulfoxide (DMSO) and dimethylformamide.

Experiments have determined that skin permeability of cannabis is relatively low. Thus, simultaneous increase in permeability and rate control may be most effectively accomplished through the use of permeation enhancers. Enhancers may be conveniently incorporated into the above-described cannabis preparation 14 and function as a replacement for the rate control membrane 15. Alternatively, the enhancers may be part of the polymer matrix composition 22. Still further, the enhancers may be blended into the adhesive layers that directly contact skin. Other techniques for controlling the rate of cannabis delivery comprise the use of different sizes of transdermal structures or by varying the number of structures being used at one time.

For purposes of the present invention, it has been found that permeation enhancer preparations should be present in an amount of about one to fifty weight percent of the overall cannabis composition. The most effective enhancers are nonionic surfactants or solvents having an HLB value from about 6 to 30. They are selected from chemical groups of glycerol esters, polyglycerol esters, alkyl fatty acid esters, ethoxylated sorbitan esters, alcohol ethoxylates, lanolin ethoxylates, ethoxylated fatty methyl esters and alkanolamides. As used herein, the term "HLB" is a numeric expression of the ability to emulsify non-soluble ingredients in oil and water. It represents the "HydrophileLipophile Balance of an emulsifier.

Figure 3:
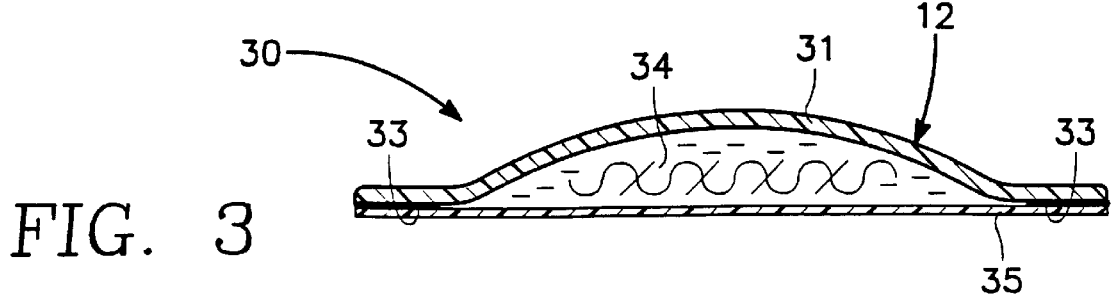
FIG. 3 is another embodiment of the invention comprising a backing layer and a reservoir containing a matrix material impregnated with cannabis and covered with a protective removable overlay.

With reference to FIG. 3, a matrix structure 30 is shown. This embodiment comprises a backing 31 having an offset portion forming a pocket or reservoir 12 to contain a porous matrix material 34 impregnated with predetermined amounts of the cannabis preparation. Around the reservoir periphery is a layer of adhesive 33. To sealingly enclose the preparation, a removable protective overlay sheet 35 is adhered to the adhesive.

The porous matrix material 34 may comprise an open pore structure such as a foamed polyurethane or sponge. In such case, the cannabis preparation will be contained within the pore structures. Alternatively, the material may include a pad of an open weave fabric such as gauze. In such case, the cannabis preparation would be held within the interstices between the fabric fibers.

The appropriate cannabis concentration must be determined on an individual basis. While cannabinoids are rarely lethal, an overdose can produce undesirable and damaging side effects. One variable that may effect the dosage of the viscous liquid or gel preparations 14 or matrix material 22, is the patient's skin permeability, which may vary twenty fold or more among individuals.

For a more effective or predictable method of transdermal delivery, the cannabinoid structure may be used in conjunction with an auxiliary means for facilitating a transdermal application. An example of an auxiliary means is the application of a patch containing a low dosage on a portion of the patient's skin containing artificially induced pores, such as those created by pin pricks.

Another auxiliary means may comprise a chemical carrier that increases the permeability of the user's skin with respect to cannabis. The chemical carrier may be incorporated into the cannabis flux, or be administered to the patient's skin as a precedent step to the cannabis application. Examples of suitable carriers include ionically charged materials, such as urea, which polarize the skin's molecules and increase the skin's permeability through ionic force. Another example is a solution of DMSO (dimethyl sulfoxide). This material may be incorporated into the cannabis preparation in volumetric concentrations of up to about ninety percent.

Figure 4:
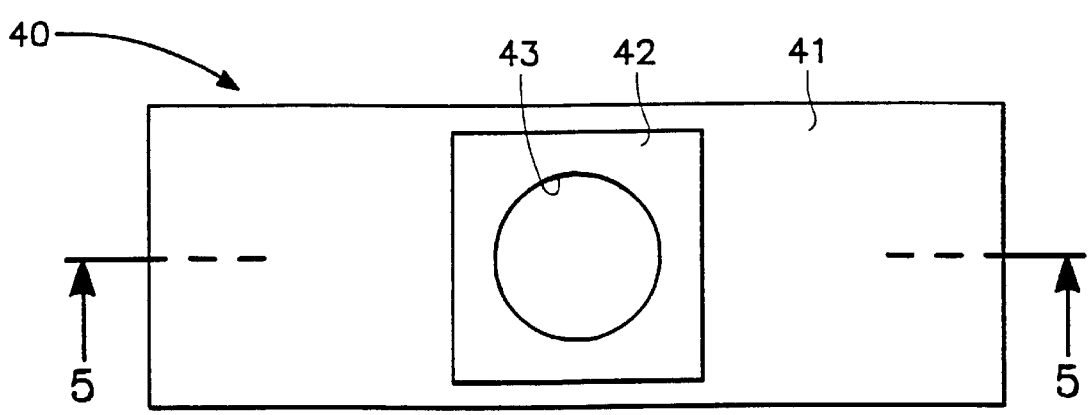
FIG. 4 is top plan view of another embodiment of the invention comprising a backing layer with a secondary overlay having an opening containing cannabis covered with a protective removable overlay.
Figure 5:
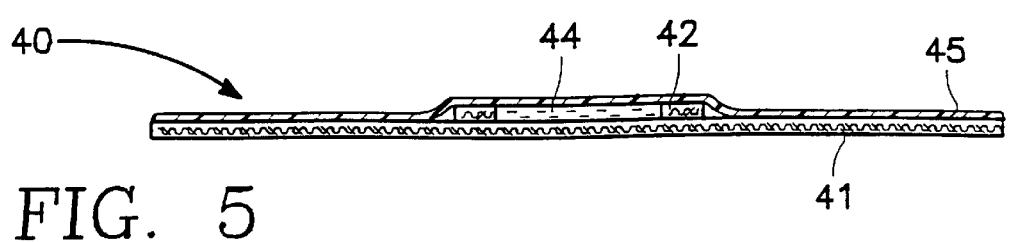
FIG. 5 is a cross-sectional view taken along lines 5—5 of FIG. 4.

FIGS. 4 and 5 illustrate an alternative laminate structure 40 which utilizes a secondary overlay to create a cannabis holding means. As shown, secondary layer 42 is fused, bonded or adhered, by means known in the art, to a larger backing strip 41. The secondary layer has an opening 43 which forms a retention cavity with the backing strip for the cannabis preparation 44. The thickness of the secondary layer and diameter of the opening will determine the maximum volume amount of preparation that can be contained within the opening.

Upper surfaces of the backing strip and secondary layer may include an adhesive film for adhering the strip to a patient's skin. A removable sheet 45, shown in FIG. 5, is used to sealingly enclose the cavity and protect the overall strip prior to use.

An example of forming the cannabis preparation involves drying and grinding to a fine powder a cannabis plant material. This powder is then refluxed with alcohol or petroleum for three to four hours to separate the cannabis oils from the plant cellulose mass. The resultant extract is further purified and concentrated by removing tars and waxes with an alcohol petroleum ether and water wash. The remaining purified oil is separated from residual solvent through distillation. Preferably, the cannabis preparation will have a Log Po/W value from five to nine.

The purified cannabis liquid is similar to honey in color and consistency. It is mixed with a carrier and any one or combination of permeation enhancer materials in selected concentrations to produce the cannabis preparation. Also, an oil may be first added to the carrier to facilitate dissolution of the cannabis components. The resultant mixture may then be optionally heated and placed within the previously described reservoir means or the mixture may be blended into a predetermined adhesive layer. Thereafter, a protective sheet may be applied and the finished assembly is packaged for storage, distribution and sale.

As indicated previously, it has been found that the overall cannabis mixture is most effective with 10–90 weight percent carrier, 1–50 weight percent active cannabis, 1–90 weight percent oil and 1–15 weight percent permeation enhancer.

Examples of effective permeation enhancer materials having an HLB from 8–10 are: PEG 200 monolaurate (Mapeg 200 MO), sorbitan monolaurate (Span 20), POE myristyl ether (Lipoco -4), POE lauryl alcohol (Ethosperse LA-4), POE lauryl ether (Brij 30), POE sorbitan monooleate (Glycosperse 0–5), octyphenoxypoly (ethyleneoxy)ethanol (Igepal CA 420), linear alcohol ethoxylate (Rexonic N4), mono and diglycerides with polysorbate 80 (Tandem 8), nonyl phenol ethoxylate (Alkasurf NP-4), alkylaryl polyether ethanol (Triton X-363 M), N,N-dimethyl amide (Mallcomid M 8–10).

Examples of effective permeation enhancer materials having an HLB from 11–14 are: PEG 400 monooleate (Alkamuls 400-MO), polyoxyaryl ether (Syn Fac 8210), POE oleyl alcohol (Ethosperse OA-9), PEG 600 monooleate (Alkamuls 600-MO), POE sorbitan monooleate (Atlas G8966T), PEG 400 monolaurate (Lipopeg 4-L), POG lauryl alcohol (Emthox 5967) and nonylphenoxypoly-(ethyleneoxy)ethanol (Igepal CO-720).

Examples of permeation enhancer materials having an HLB from 15–28 are: nonyl phenol ethoxylate (Alkasurf NP-15), castor oil ethoxylate (Sandoxylate C-32), ethoxylated cocomonoglyceride (Varonic LI-63), oleylalcohol condensed with ethylene oxide (Volpo-20), modified oxyethylated straight chain alcohol (Plurafac C-17), ethoxylated lanolin alcohol (Polychol 40), nonylphenyl ethoxylate (Alkasurf NP-30), polyethylene 100 stearyl ether (Brij 700), PEG 6000 monooleate (Kesso Polyethylene Glycol Esters), ethoxylated polyoxypropylene glycols (Alkatronic PGP 23–7) and ethoxylated polyoxypropylene glycols (Alkatronic PGP 23–8).

Examples of adhesive materials that may also function as a matrix to carry the active cannabis and enhancer preparations are acrylic adhesives from 3M such as 9871 Cotran neutral function pharmaceutical grade transfer adhesive, 9872 Cotran acid function pharmaceutical grade transfer adhesive and PSA 55236 acrylate copolymer. Useful acrylic adhesives from National Starch and Chemical Products are Duro-Tak 87-2516, 87-2677 and 87-2196. Other effective adhesives are polyisobutylene/light mineral oil:Oppanol B100/B10 blend 1:2 (BASF), Bio-PSA Q7-2920, 355 Medical adhesive (Dow Corning), polystryene-polybutadiene block copolymer/mineral oil:Kraton thermoplastic elastomers (Shell Corp.) and hydrogel:Methocel products (Dow Chemical).

Attributes of the cannabis structures and methodology described herein are:
1) Daily amounts of cannabis to be administered through intact skin range from about 0.25 to 10 micrograms per hour.
2) The extended period of time for cannabis administration is from one through seven days.
3) The area of intact skin through which the cannabis is administered may range from about 5 to 100 square centimeters.
4) The rate at which cannabis may be administered may range from about 0.5 to 20 micrograms per square centimeter per hour.

In a test with two subjects, a structure similar to FIG. 2 was prepared using about 0.2 gram of cannabis solution and about 0.02 grams of DMSO. The structure was applied to the underside of the wrist of two human subjects. In about ten minutes, the soothing affect of the medication was observed. No side effects were detected and the affects of the cannabis were felt for four to six hours.

EXAMPLES OF CANNABIS FORMULATIONS AND STRUCTURES

A. Cannabis Patch With a Rate-Controlling Membrane

The cannabis formulation is prepared with a total of 10 percent of a selected cannabinoid mixture in the drug formulation (comprising delta 8 THC 3%, delta 9 THC 30%, cannabidiol 35% and cannabinol 32%). The cannabinoids are dispersed in the USP grade light mineral oil (Penta Mfg.), and a mixture of N,N-dimethyl amide (Hallcomid M 8-10) and linear alcohol ethoxylate (Rexonic N4) in equal proportion (total of 20% of formulation) is dispersed also in the formulation. The formulation is then gelled for ease of processing by using silica particles (3% of formulation) (Spectrum Lab. Products). The permeation enhancing compounds are incorporated to increase skin permeability to the cannabinoids and to control the flux of cannabinoids through the skin.

A drop of the gelled formulation is metered on a piece of a backing film (1006 Scotchpak polyester film laminate, 3M) in the amount of 300 mg per square centimeter and covered with a tri-laminate consisting of three films (Adhesives Research), namely, a porous membrane/acrylic adhesive/release liner with the porous membrane side facing the gel. The tri-laminate and the backing film were then heat-sealed using an impulse heat sealer into a circular configuration to form a reservoir. The size of the heat-sealed area was approximately 2.5 square centimeters. The porous membrane was 9711 Cotran film (3M), the acrylic adhesive is Dur0-Tak 87-2516 (national Starch and Chemical) and the release liner 1022 Scotchpak (3M). Following the heat-sealing step, a cannabis patch is fabricated by trimming the edges outside of the heat-sealed area.

To determine in-vitro permeation rates of various cannabinoids from the cannabinoid patch, the release liner is removed from the patch and the adhesive surface is attached to the stratum corneum side of a human cadaver epidermis. The patch/human epidermis assemblies are then inserted into Franz skin permeation cells (Vertical type from Hanson Research), with the receptor compartments filled with an aqueous solution containing 20% ethanol as a cannabinoid solubilizer. The epidermis side of the skin is in contact with the receptor solution. The complete Franz cells are kept in an environment at 37 degree Celsius for seven days. Each day the receptor compartment is drained and the receptor solution is assayed for selected cannabinoids. It is refilled with a fresh portion of ethanolic water solution. The process is continued for seven full days.

The assay values of various cannabinoids and time intervals reveal that the overall skin flux of cannabinoids is 15 micrograms per square centimeter per hour (individual cannabinoid fluxes are delta 8 THC 0.45, delta 9 THC 4.5, CBD 5.25 and CBN 4.8 micrograms per square centimeter per hour). A control patch that does not have any skin permeation enhancers, but is otherwise an identical cannabis patch, indicates a skin permeation rate of total cannabinoids at approximately 0.1 microgram per square centimeter per hour. The ratio between different cannabinoids is similar to the compositions in the control patch formulation.

The cannabis patch fabricated in this Example may effectively deliver the cannabinoids for 7 days. The patch size can be as small as 0.69 square centimeter (for daily dose of 0.25 mg) and as large as 27 square centimeter for a daily dose of 10 mg.

B. Cannabis Patch With Adhesive Matrix Reservoir

A cannabis formulation is prepared from Duro-Tak 87-2516 as an adhesive matrix material. A total of 20% (on dry basis) of the same cannabinoids in the same ratios as Example A, is suspended in the matrix formulation along with two permeation enhancers, polyoxyaryl ether (Syn Fac 8210) and nonyl phenol ethoxylate (Alkasurf NP-15). The two permeation enhancers are present in a 50/50 ratio and amount to approximately 15% of the adhesive matrix material (dry basis).

The cannabinoids and permeation enhancers are added to, and thoroughly mixed in the Duro-Tak solution at room temperature. The adhesive drug solution is cast on 1109 Scotchpak backing film (3M) so that, when dried in an oven at 60 Celsius for 30 minutes, a dry adhesive matrix of 0.006 inch was obtained on the backing film. The 9747 Scotchpak release liner (3M) is laminated on the adhesive matrix surface under 30 pounds per square inch pressure. The tri-laminate consisting of the backing, the adhesive matrix and the release liner are die-cut using a steel rule die to complete the patch fabrication. As in Example A, the size of patch is 2.5 square centimeter for determining in-vitro drug skin permeation rate.

The cannabis patches are tested using the same method as in Example A. Total skin flux of combined cannabinoids was approximately 25 micrograms per square centimeter per hour.

To deliver 10 mg of the combined cannabinoids per day, one patch covering an area of 17 square centimeters will be required. When constructed as above described, the patch will be effective for a three-day delivery of the selected cannabinoids.

C. Cannabis Patch With A Foam Preform As A Reservoir

The cannabis patch structure is similar to Example B except that the backing is aluminum foil and the drug formulation is contained in a pre-formed piece of low density polyethylene open pore foam. Also, the patch will not have an in-line adhesive layer, but an adhesive layer about the backing edges.

A small cavity is formed in a piece of aluminum foil (0.005 inch thick, American National Can). A peripheral adhesive layer, with its protective release liner still on, is laminated in a circular configuration around the cavity. Into the cavity is inserted a matching piece of low density polyethylene foam (American Excelsior). The foam is secured with a cyanoacrylate glue. The drug formulation set forth in Example A is impregnated into the foam until the open pores of the foam are filled with the formulation. The original release liner is removed from the peripheral adhesive and a new liner is applied over the adhesive and foam.

Patches made in the above manner are evaluated for skin irritation in human volunteers. Following removal of the release liner, the patches are applied to the forearm of volunteers continuously for three days. The overall patch size is 2.5 square centimeter and the effective surface area of the drug reservoir is about 2.0 square centimeter. Each one of seven volunteers wore two patches, one on each forearm. After three days, the sites where the patches were applied was examined for any dermatological symptoms for three days. No clinically unacceptable skin reactions were observed at the patch application sites in all seven volunteers. (Darize score of 1.5 out of possible maximum of 8 was achieved).

The in-vitro skin permeation tests using the same method as in Example A were carried-out for the patches fabricated in the Example. The skin flux of approximately 17 micrograms per square centimeter per hour was obtained through human cadaver epidermis tissues at 37 degree Celsius. The skin permeation rate of the cannabinoids suggest that the patches of this Example are equivalent to those of Example A in terms of cannabinoid delivery through human skin.

While the invention has been described with respect to preferred embodiments, it will be clear to those skilled in the art that modifications and improvements may be made to the invention without departing from the spirit and scope of the invention. Therefore, the invention is not to be limited by the specific illustrative embodiments, but only by the scope of the appended claims.

We claim:

1. A method of delivering cannabis to the bloodstream of a person comprising the steps of:
   A. Providing a transdermal preparation comprising 1–50 weight percent cannabis and 1–15 weight percent skin permeation enhancer;
   B. Providing a backing layer selected from the group consisting of a patch, strip, bandage and covering for holding said transdermal preparation;
   C. Placing an effective amount of said transdermal preparation onto said backing layer; and,
   D. Attaching said backing layer to the skin of said person so that said transdermal preparation is in contact with said skin.

2. The method of claim 1 wherein step A comprises combining said cannabis with about 10–90 weight percent transdermal carrier.

3. The method of claim 2 wherein said transdermal carrier comprises a member selected from the group consisting of natural rubber, viscoelastic semi-solid materials, hydrogels, thermoplastic polymers, elastomers and thermoplastic elastomers.

4. The method of claims 3 wherein said transdermal carrier includes an oil selected from the group consisting of mineral oils, vegetable oils, fish oils, animal oils, carbon tetrachloride, ethanolic solutions of resins and pyrahexyl mixtures.

5. The method of claim 1 wherein said skin permeation enhancer has an HLB of about 6–30.

6. The method of claim 1 comprising the additional steps of:
   providing an adhesive mixture containing an effective amount of said transdermal preparation; and,
   carrying out step C by applying said adhesive mixture onto said backing layer.

7. The method of claim 1 comprising the additional step of providing a reservoir means to said backing layer for holding said transdermal preparation.

8. The method of claim 7 wherein said reservoir means is any one or combination of a member of the group consisting of a cavity, matrix material, adhesive layer and film.

9. The method of claim 1 wherein after step D, maintaining said transdermal preparation in contact with said skin for an effective period of time.

10. The method of claim 1 wherein said cannabis has a Log Po/w value from 5 to 9.

11. A cannabis transdermal delivery structure comprising:
    a backing layer selected from the group consisting of a patch, strip, bandage or covering;
    said backing layer having a transdermal preparation comprising 1–50 weight percent cannabis, 10–90 weight percent carrier and 1–15 weight percent skin permeation enhancer.

12. The structure of claim 11 wherein said transdermal preparation includes 1–90 weight percent oil.

13. The structure of claim 11 wherein said skin permeation enhancer has a HLB of about 6–30.

14. The structure of claim 11 wherein said backing layer includes a reservoir means for holding said transdermal preparation.

15. The structure of claim 14 wherein said reservoir means is any one or combination of a member of the group consisting of a cavity, matrix material, adhesive layer and film.

16. The structure of claim 15 wherein said matrix material is selected from the group consisting of an open pore material, open weave fabric and a membrane.

17. The transdermal structure of claim 14 wherein said reservoir means comprises a convex portion of said backing layer.

18. The structure of claim 11 wherein a secondary layer is attached to said backing layer, said secondary layer having an opening which forms a retention cavity with said backing layer for holding said transdermal preparation.

19. The structure of claim 11 wherein said cannabis has a Log Po/w value from 5 to 9.

20. A structure for administering cannabis to skin, comprising:
   at least one layer of backing material suitable for attachment to said skin; and,
   a cannabis preparation on said backing material comprising 1–50 weight percent cannabis, 10–90 weight percent carrier and about 1–15 weight percent permeation enhancer.

21. The structure of claim 20 wherein said permeation enhancer has a HLB of 6–30.

22. The structure of claim 21 wherein said carrier includes about 1–90 weight percent oil.

23. The structure of claim 22 wherein said oil is a member selected from the group consisting of mineral oil, vegetable oil, fish oil and animal oil.

24. The structure of claim 20 wherein said backing material is any one or combination of a member selected from the group consisting of fabric, plastic, metal foil, rubber, resin film and membrane.

25. The structure of claim 20 wherein said backing material includes a reservoir means for retaining said cannabis preparation.

26. The structure of claim 25 wherein said reservoir means comprises a member selected from the group consisting of cavity, matrix material, adhesive layer and film.

27. The structure of claim 25 wherein said reservoir means includes a rate control means for regulating the flow of said cannabis preparation to said skin.

* * * * *